US012797146B2

(12) United States Patent
Zhao et al.

(10) Patent No.: US 12,797,146 B2
(45) Date of Patent: Nov. 17, 2026

(54) MIS ROBOTIC CONTROL TERMINAL AND ROBOT SYSTEM

(71) Applicant: Hefei University of Technology, Hefei (CN)

(72) Inventors: Ping Zhao, Hefei (CN); Xu Han, Hefei (CN); Bing Chen, Hefei (CN); Zelong Wu, Hefei (CN); Xuanqing Huang, Hefei (CN)

(73) Assignee: Hefei University of Technology, Hefei (CN)

( * ) Notice: Subject to any disclaimer, the term of this patent is extended or adjusted under 35 U.S.C. 154(b) by 620 days.

(21) Appl. No.: 17/966,475

(22) Filed: Oct. 14, 2022

(65) Prior Publication Data

US 2023/0233278 A1 Jul. 27, 2023

(51) Int. Cl.

*A61B 34/37* (2016.01)
*A61B 34/00* (2016.01)
*A61B 17/00* (2006.01)

(52) U.S. Cl.

CPC .............. *A61B 34/37* (2016.02); *A61B 34/74* (2016.02); *A61B 2017/00477* (2013.01)

(58) Field of Classification Search

CPC .................... A61B 34/37; A61B 34/74; A61B 2017/00477; A61B 90/50; A61B 2017/00973; A61B 34/30; A61B 34/76; A61B 2034/301; A61B 2034/305; A61B 2034/742; A61F 9/008

See application file for complete search history.

(56) References Cited

U.S. PATENT DOCUMENTS

2014/0324070 A1* 10/2014 Min ........................ A61B 34/30 606/130
2018/0049818 A1* 2/2018 Yates ..................... A61B 34/37
2020/0022761 A1* 1/2020 Cone ...................... A61B 34/35

FOREIGN PATENT DOCUMENTS

CN 113648066 A * 11/2021 ............ G01B 11/14
EP 3412241 A1 * 12/2018 ............ A61B 34/25
KR 20140129702 A * 11/2014 ............ A61B 34/30

* cited by examiner

*Primary Examiner* — Alyssa M Alter
(74) *Attorney, Agent, or Firm* — Smart & Biggar LP

(57) ABSTRACT

A MIS robotic control terminal and robot system, comprising: a master manipulator handle, for driving at least one slave manipulator coupled thereto; a display-and-control portion, for controlling the master manipulator handle and the at least one slave manipulator coupled to the master manipulator handle; and a foot operated clutch portion, for breaking signal communication between the master and slave manipulators; in which when a human operator uses the display-and-control portion to establish signal communication between the master manipulator handle and any slave manipulator, the display-and-control portion is at least capable of according to types of instruments on two slave manipulators that are currently in communicative connection to master manipulator handles that are different from each other, respectively, defining a moving space of any slave manipulator in a corresponding surgical area by calling movement schemes corresponding to the types of the instruments.

8 Claims, 4 Drawing Sheets

MIS ROBOTIC CONTROL TERMINAL AND ROBOT SYSTEM

BACKGROUND OF THE INVENTION

1. Technical Field

The present invention relates to devices for medical operations, and more particularly to a robotic control terminal and robot system to be used in minimally invasive surgery (MIS).

2. Description of Related Art

Surgical robots represent a successful example of robotic and medical surgical technologies, which enables surgeons to conduct surgical operations when close contact is impossible and improves working conditions for minimally invasive surgery. Therefore, studies on surgical robots have attracted increasing attention from scientists and researchers.

CN104382689A discloses a femtosecond laser system for imaging and operation at the same time. The system comprises a sample module, a femtosecond laser operation module and a secondary harmonic signal imaging module. The femtosecond laser operation module is used for the femtosecond laser cutter to conduct femtosecond laser cornea cutting operations and is provided with a femtosecond laser oscillator. The laser light source generated by the femtosecond laser oscillator is irradiated to the sample of the sample module to generate a secondary harmonic signal, and the secondary harmonic signal imaging module collects the secondary harmonic signal to perform imaging so as to observe femtosecond laser cornea cutting effect. The femtosecond laser system is applicable to actual operations, the femtosecond laser cornea cutting effect can be observed clearly, and large modification of existing operation systems is not needed.

Oral surgery as a branch of medical operations features restricted operational space and high operational precision. Currently, research of designs of robots for oral surgery is in its infancy and thus related control consoles are less developed. The existing control consoles are structurally complicated, expensive to manufacture and inferior in terms of human-machine interaction. As unreasonable designs of control consoles for surgical robots can be detrimental to surgical precision, it is desirable to solve the above and more technical problems seen in the prior art.

In addition, on the one hand, due to the differences in the understanding of those skilled in the art; on the other hand, due to the fact that the applicant studied a large amount of literature and patents when putting the invention, but space limitations do not allow all the details and content are described in detail, however, this does not mean that the invention does not have these prior art features, on the contrary, the present invention already has all the features of the prior art, and the applicant reserves the right to add relevant prior art to the background technology.

SUMMARY OF THE INVENTION

In view of the shortcomings of the prior art, the present invention provides an MIS robotic control terminal and robot system, which feature structural simplicity, functional maturity, and human-engineering-conformable constituent components, improving operational comfort for doctors and enhancing operational precision when close contact is impossible, so as to solve one or more technical problems seen in the prior art by.

To achieve the foregoing, the present invention provides a MIS robotic control terminal and robot system, comprising at least.

a foot-operated clutch portion, for breaking signal communication between the master and slave manipulators;

a master manipulator handle, for driving at least one slave manipulator coupled thereto; arm supports, which are movably coupled to the master manipulator handles, and are used to receive and perform postural adjustment to arms of a human operator;

a display-and-control portion, for controlling the master manipulator handle and the at least one slave manipulator coupled to the master manipulator handle;

a multi-axis robotic arm, which is in communicative connection to the display-and-control portion in a manner that adjusts its own spatial location when driven by the display-and-control portion; and a display screen, which is coupled to the multi-axis robotic arm and is used to display images in a surgical area in a mouth cavity of a patient in a real-time manner.

Preferably, when a human operator uses the display-and-control portion to establish signal communication between the master manipulator handle and any said slave manipulator, the system is at least capable of according to types of instruments on two said slave manipulators that are currently in communicative connection to master manipulator handles that are different from each other, respectively, defining a moving space of any said slave manipulator in a surgical area by means of calling movement schemes corresponding to the types of the instruments. For surgical operations conducted under difficult conditions yet demanding in precision, such as minimally invasive oral surgery, since the space inherently defined by an oral cavity is limited, movements of surgical instruments have to be controlled severely in terms of both moving pattern and path, or physical and functional interference between surgical instruments tend to happen. For example, physical interference like collision can lead to damage to surgical instruments and the broken parts can cause injuries to oral tissues of patients. In the present invention, when a human operator drives different surgical instruments on slave manipulators to move and perform corresponding surgical operations, the system calls and uses pre-configured movement schemes corresponding to the currently used slave manipulators from a system database according to the actual types of devices on the slave manipulators, to plan or limit the moving space of each slave manipulator in the oral cavity of the patient, thereby preventing the slave manipulators from causing physical or functional interference to each other that degrades surgical performance and even cause personal injuries. Secondary, for human operators not proficient in operations of instruments and device, the present invention provides an objective and passive way to limit the operational range or space that they operate the surgical instruments on the slave manipulators to move. This not only helps reduce the risk of surgical incidents, but also provides knowledge of regulations for surgical operations and for use of devices by presenting interactive moving spaces and/or spacing when the slave manipulators move around for operators to learn or review. Particularly, practitioners lacking for experience in large surgery can get help and guide that are useful for them to follow and conduct surgery safely in a reasonable operational space. In addition, when an inexperienced or unpracticed human operator uses a robot for oral surgery to conduct corresponding surgical simulation or experiments, he/she can call configuration schemes for slave manipulators from other operators for similar operations through the control console of the present invention as references or templates.

Preferably, when a human operator uses the display-and-control portion to control any two said slave manipulators that are in communicative connection to master manipulator handles that are different from each other, respectively, to move, the moving spaces of the two current slave manipulators allowable by the system are kept within moving intervals and/or moving areas provided by the movement schemes corresponding to the types of the instrument.

Preferably, when a human operator uses the display-and-control portion to control any two said slave manipulators that are in communicative connection to master manipulator handles that are different from each other, respectively, a travel speed of any of the slave manipulators allowable by the system is associated with the spacing between the slave manipulator and the other slave manipulator, and the travel speed changes gradually in a linear/non-linear manner with change in a spatial distance between the any two said slave manipulators. Particularly, different types of devices connected to the slave manipulators may bring about different levels of risk or damage due to their respective natures. In the present invention, slave manipulators are divided by risk levels corresponding to their types, so as to facilitate human operators or doctors configuring surgical schemes correspondingly and planning and controlling movements of corresponding slave manipulators. This allows strict control of operations of various surgical instruments and their relative spatial locations in minimally invasive oral surgery, thereby minimizing the risk of damage to instruments, devices, and systems, reducing the probability of surgical incidents, and in turn enhancing surgical efficiency and effects. Meanwhile, for different types of surgical instruments, their moving spaces and spacing are planned according to actual needs, so as to ensure precise control of various surgical instruments, thereby preventing unexpected damage to instruments and injuries to medical staff caused by improper use of surgical instruments.

Preferably, the master manipulator handle comprises a first operating handle and a second operating handle provided on a top of the control console such that the first operating handle and/or the second operating handle is configured to have its central axis angled with respect to an edge of the top at a predetermined angle.

Preferably, a first operating handle and/or a second operating handle is coupled to at least one slave manipulator. Therein, the at least one slave manipulator comprises forceps, femtosecond laser cutters, and/or endoscopes.

Preferably, a foot-operated clutch portion is deposited at a bottom of the control console at the opposite side to where a human operator operating the control console is supposed to locate. Therein, the foot-operated clutch portion comprises:

a first master handle communication control pedal, for breaking signal communication between the first operating handle and at least one slave manipulator coupled thereto;

a second master handle communication control pedal, for breaking signal communication between the second operating handle and at least one slave manipulator coupled thereto;

a laser cutter control pedal, for breaking signal communication between the femtosecond laser cutter and the first operating handle or the second operating handle coupled thereto; and an emergency stop pedal, for immediately braking the whole control system.

Preferably, the at least one slave manipulator coupled to and driven by the first operating handle includes at least a pair of forceps;

the at least one slave manipulator coupled to and driven by the second operating handle includes a femtosecond laser cutter and an endoscope; and at least one slave manipulator acting as a terminal executor coupled to a corresponding slave manipulator robotic arm.

Preferably, the arm supports are coupled to the master manipulator handle and the top of the control console such that the arm supports are rotatable about the master manipulator handles, in which, the arm support comprises a support pole and an arm bracket that are coupled to each other, wherein the support pole has its end distant from the arm bracket coupled to the top of the control console, and the arm bracket has its end distant from the support pole coupled to the master manipulator handle.

Preferably, the arm bracket is at least partially configured to have a recess matching the contour of an arm of an average human operator, so that the recess can receive and support an arm of a human operator.

Preferably, the display-and-control portion is arranged on the top of the control console, and comprises:

a first support post and a second support post that are movable and are coupled to each other; and a touch screen that provides functions about process control and display;

wherein the first support post is coupled to the top of the control console, and the touch screen is deposited at an end of the second support post.

Preferably, the multi-axis robotic arm is provided on the top of the control console, and includes a plurality of mechanical shafts that are coupled to each other and are to be driven independently, so that the multi-axis robotic arm is capable of moving with at least three degrees of freedom in response to a driving instruction given by the display-and-control portion.

Preferably, a storing slot is formed on the top of the control console for fittingly receiving a touch screen, so that when the system is not in use, the touch screen can be stored in the storing slot by means of a movable first support post and a movable second support post that are coupled thereto. The present invention is highly integrated, compact, and highly human-machine interactive. When a human operator performs minimally invasive oral surgery using the system of the present invention, he/she can conveniently and rapidly set working positions of various surgical instruments, and can freely adjust the relative spatial locations between the display device and himself/herself, thereby satisfying his/her visual preference and operational habit and providing them a relative comfortable working environment, which allows a human operator to work with less pressure and enhances surgical efficiency and safety. Furthermore, with increased coordination among components, when the human operator is busy, synergy between his/her limbs and the brain can be maximized in virtue of the positional relationship among operative ends of the control console. This not only improves working efficiency but also minimizes risk of personal injuries to medical staff and patients during surgery.

Preferably, the foot-operated clutch portion comprises an intrinsic safety braking portion for performing braking operations on intrinsic safety operations and a security braking portion for performing braking operations on dangerous operations, and the intrinsic safety braking portion and the security braking portion are configured to each have at least one neutral position in addition to an on position and an off position, in which the security braking portion is to be switched among the on position, the off position, and the at least one neutral position based on corresponding states determined by the display-and-control portion, so that the security braking portion at the at least one neutral position is capable of performing the cut operations different from the cut operations for the dangerous operations related to the off position; and the intrinsic safety braking portion is to be switched among the on position, the off position, and the at least one neutral position by an external-force operation different from an operation that switches it to the off position, so that the intrinsic safety braking portion at the at least one neutral position is capable of performing the braking operations different from the braking operations on the intrinsic safety operations related to the off position.

Preferably, the display-and-control portion, in response to that at least one said master manipulator handle is switched from a first operation not related to laser operations to a second operation related to laser operations, or in response to that at least one said master manipulator handle performs the second operation related to laser operations, switches the corresponding intrinsic safety braking portion of the foot-operated clutch portion to the neutral position where the intrinsic safety braking portion is in a first activated state where the intrinsic safety braking portion is in a to-be-activated state, and/or switches the corresponding security braking portion of the foot-operated clutch portion to the neutral position where the security braking portion is in a second activated state where the security braking portion is in an activated-standby state.

The present invention creatively divides the foot-operated clutch portion into an intrinsic safety braking portion and a security braking portion. Therein, the intrinsic safety braking portion used to perform braking operations on intrinsic safety operations and the security braking portion used to perform braking operations on dangerous operations each have at least one neutral position. At the neutral position, the system records positions, travels, and postures of various moving components with higher frequency and precision. Thereby, at the neutral position, when an operator presses a corresponding pedal with significantly increased speed or depth, the intrinsic safety braking portion can record the current travel, position, and/or posture while braking the master manipulator handle coupled to the slave manipulator (e.g., a robot gripper), so as to significantly reduce the rebooting time after stop, thereby saving the patient on the operating table from futile waiting.

Furthermore, when the security braking portion is in the neutral position, the system is electrically well prepared to stop the femtosecond laser device in any minute by, for example, disconnecting electrical components irrelevant to the current surgical operation in terms of circuit, so as to protect these electrical components from in-rush currents in case of emergency stop. Without such a protective approach, some of these electrical components may be disrupted because a femtosecond laser cutter has a very high instantaneous power, and its sudden stop is destructive if it is not pre-connected a discharge bypass (such as a voltage reducing channel equipped with a tail current diode). For example, for replacing a blown fuse, a time-out for at least ten minutes has to be called during surgery, which introduces additional risk of surgical fault and infection (by, for example, a maintenance technician entering the operating room). Furthermore, having the central control unit of the system disconnect electrical components irrelevant to the current surgical operation in advance also helps reduce inertia faults of the circuits and minimize the downtime. This is of a huge value to enhance the safety of high-risk surgery like femtosecond laser surgery.

DETAILED DESCRIPTION OF THE INVENTION

The present invention will be described in detail with reference to the accompanying drawings, FIG. 1 through FIG. 5.

Figure 1:
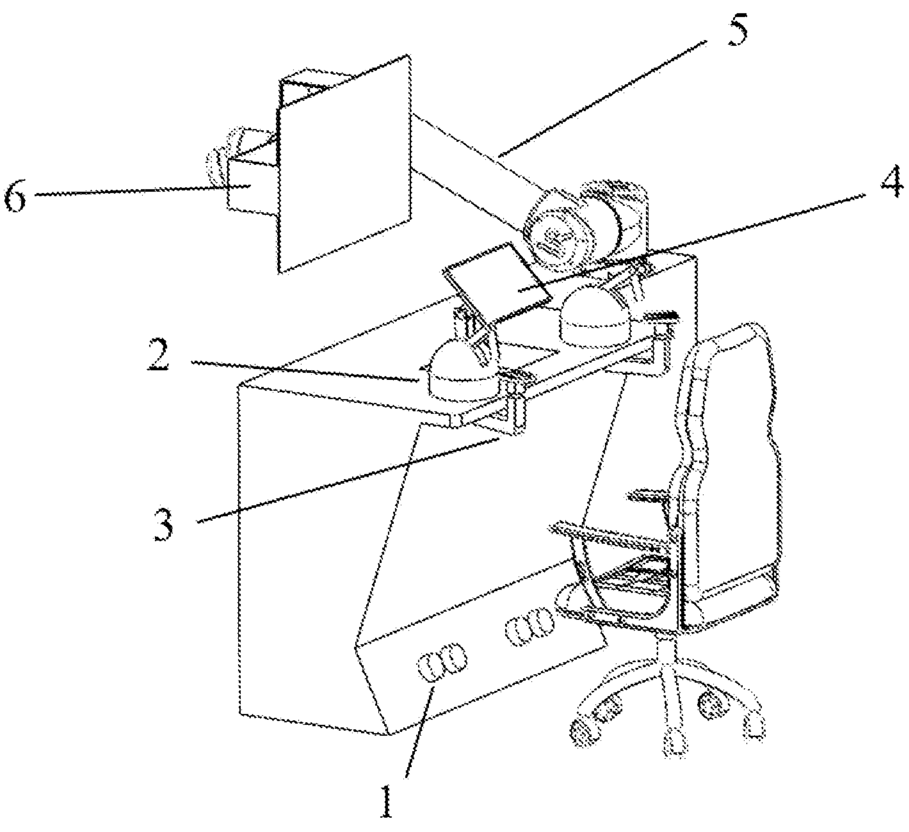
FIG. 1 is a schematic applied view of an MIS robotic control terminal and robot system according to a preferred mode of the present invention.
Figure 2:
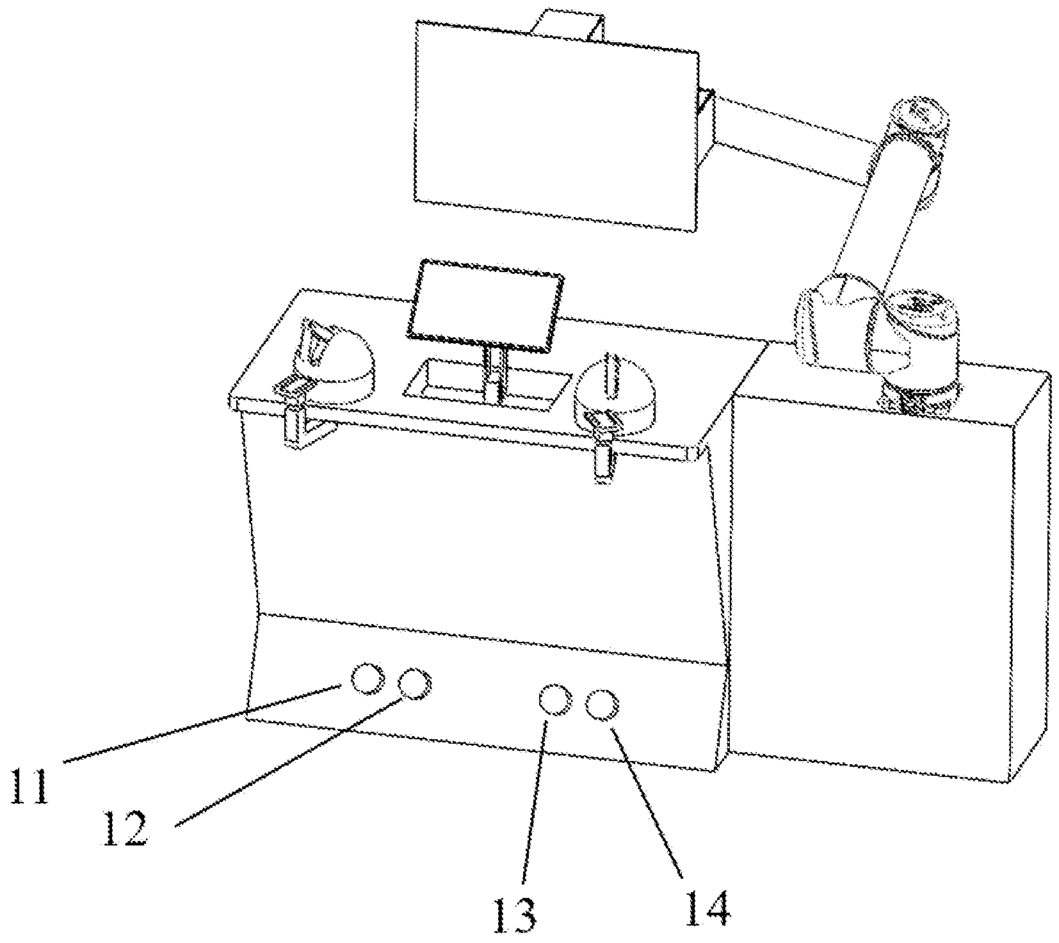
FIG. 2 is another schematic applied view of the MIS robotic control terminal and robot system according to a preferred mode of the present invention.

The present invention provides an MIS robotic control terminal and robot system, as shown in FIG. 1, the control terminal or the system may be embodied as a control console designed especially for controlling robots to conduct femtosecond-laser-based minimally invasive oral surgery. Specifically, as shown in FIG. 1 and FIG. 2, the control terminal or system may comprise at least one of the following components:

a foot-operated clutch portion 1, located at the bottom of the control console, for breaking signal communication between the master and slave manipulators;

a master manipulator handle 2, comprising at least two operating handles symmetrically arranged on the top of the control console, for controlling or driving at least one slave manipulator coupled thereto;

an arm support 3, movably coupled to the master manipulator handle 2 and the top of the control console, so that it is rotatable in the plane where the top of the control console is located;

a display-and-control portion 4, deposited on the top of the control console, and at least used to establish signal communication between the master manipulator handle 2 and the at least one slave manipulator;

a multi-axis robotic arm 5, deposited at one side of the top of the control console, and being in communicative connection with the display-and-control portion 4, so that the spatial location of the robotic arm 5 can be controlled through the display-and-control portion 4; and a display screen 6, coupled to the end of the robotic arm 5, for displaying images in a surgical area in an oral cavity of a patient in a real-time manner.

According to one preferred mode, as shown in FIG. 2, the foot-operated clutch portion 1 may comprise a first master handle communication control pedal 11, a second master handle communication control pedal 12, a laser cutter control pedal 13, and an emergency stop pedal 14. The pedals are separated and arranged at the bottom of the control console. Preferably, the first master handle communication control pedal 11, the second master handle communication control pedal 12, the laser cutter control pedal 13, and the emergency stop pedal 14 are such orientated that a doctor operating the system can use them conveniently.

Particularly, in the prior art, emergency stop is usually embodied by a hand brake. However, a doctor busy at surgical operations tends to have both of his/her hands occupied and become unable to conduct any additional manual operation. Sometimes, there may be surgical patients necessitate frequent operations performed by both hands of a doctor. In this case, when sudden incidents happen, doctors may fail to spare a hand timely to operate a corresponding device to trigger a time-out. In the present invention, a trigger for emergency stop is embodied as a foot-operated pedal installed near the feet of a human operator instead of the conventional hand brake. Thereby, operative pressure effecting on the hands and the brain of the operating doctor can be properly eased. In the event of a sudden incident, the operating doctor can easily stop the control console and the corresponding surgical instruments by simply pressing the corresponding emergency stop pedal, making the system respond to sudden incidents timelier. Doctors thus can respond to sudden incidents simply and promptly, and the foot-operated means helps prevent mis-operations under hurry-scurry that endanger both the medical staff and the patients like wrongly pulling the hand brake or unintentionally moving surgical instruments that are working.

It is known that femtosecond laser works at extremely high energy, with its instantaneous power as high as 100 MW, many folds higher than normal laser/rays or other energy entities. Thus, femtosecond laser can cause much more serious and lethal injuries as compared to other instruments, like forceps. A femtosecond laser cutter should be used with special care and particularly it should be strictly controlled in terms of output power and output period and/or frequency. Besides, minimally invasive oral surgery is conducted in a special environment because oral tissues are highly vulnerable and contains numerous important nerves, cells, bones, and muscles. Therefore, use of a femtosecond laser cutter in minimally invasive oral surgery needs top-priority control. The present invention thus provides a laser cutter control pedal 13 dedicated to control communication and operations of a femtosecond laser cutter, thereby accelerating operational responses of the femtosecond laser cutter and minimizing safety risk related to use of femtosecond laser. Preferably, the laser cutter control pedal 13 is located at the same side as the emergency stop pedal 14. This helps reduce mis-operations because when the left and right cerebral hemispheres instruct right and left sides of the trunk to perform different actions, spontaneous imitation and interaction between the two sides can always happen. For example, it is believed that drawing a circle with the right hand and drawing a square with the left hand simultaneously is impossible to be done simultaneously because this is against the logical thinking and control that a human brain conducts. Given this knowledge, it is imaginably that when a doctor operating the system frequently presses the pedals with his/her right foot, his/her left foot may unconsciously follow this action. With the laser cutter control pedal 13 and the emergency stop pedal 14 arranged at two sides, either of them might be triggered unintentionally and wrongly, leading to great danger. By having the two pedals arranged at the same side of the operator, the risk of the foregoing mis-operations can be minimized because there is less likely to make a mistake when the unilateral leg is driven by the brain to perform the corresponding action. Preferably, controls of the endoscope and other low-risk instruments can be grouped at one side, while controls of the femtosecond laser cutter and other high-risk instruments can be grouped at the other side.

According to one preferred mode, first master handle communication control pedal 11 may be used to break signal communication between the first operating handle deposited at one end of the top of the control console and at least one slave manipulator coupled thereto. The second master handle communication control pedal 12 may be used to break signal communication between the second operating handle that is symmetrical to the first operating handle and deposited at the other end of the top of the control console and at least another slave manipulator coupled thereto. The laser cutter control pedal 13 may be used to break signal communication between the femtosecond laser cutter and the first operating handle or the second operating handle coupled thereto. The emergency stop pedal 14 is used to trigger emergency stop.

According to one preferred mode, as shown in FIG. 1 and FIG. 2, the master manipulator handle 2 may include two operating handles that are arranged symmetrically with respect to the top of the control console. Preferably, the operating handle may be a touch handle. Particularly, when a human operator naturally puts his/her arms on the top of the control console, his/her arms are not perpendicular to the edge of the top of the console. To ergonomically fit the natural postures and profiles of arms of a human operator who naturally rests his/her arms on the console top, the master manipulator handles 2 are angled with respect to a line perpendicular to the edge of the console top by a predetermined angle. For example, the angle may be 15°-30°.

Further, for easy understanding, the operating handles deposited at the first end (e.g., the left end) of the top of the control console first is defined as the first operating handle, and the other operating handle deposited at the second end (e.g., the right end) of the top of the control console first is defined as the second operating handle. The first operating handle and the second operating handle are each coupled to at least one slave manipulator (not shown in the figures.). The slave manipulator is a surgical instrument, and each surgical instrument as an end executor is coupled to a corresponding slave manipulator robotic arm. Specifically, the slave manipulator coupled to and driven by the first operating handle through the display-and-control portion 4 may include two pairs of forceps, and the slave manipulator coupled to and driven by the second operating handle through the display-and-control portion 4 may include a femtosecond laser cutter and an endoscope. Preferably, each slave manipulator may be controlled through the touch handle it coupled to.

Figure 3:
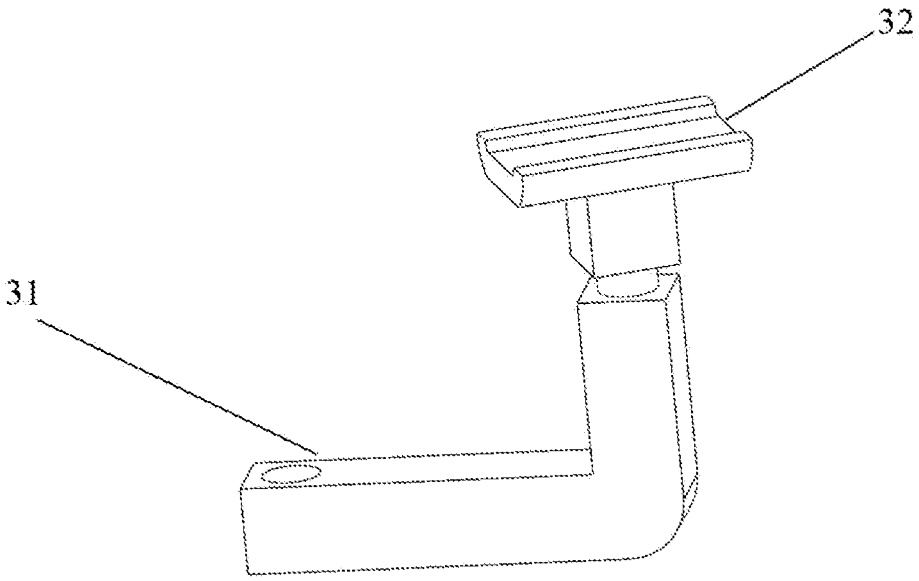
FIG. 3 is a perspective view of an arm support of the MIS robotic control terminal and robot system according to a preferred mode of the present invention.

According to one preferred mode, as shown in FIG. 1 and FIG. 2, an arm support 3 is deposited on the edge of the top of the control console to be positionally corresponding to the master manipulator handle 2. The arm support 3 is of a roughly "L" shape, and has one end coupled to the bottom of the top of the control console and the other end coupled to the master manipulator handle 2. Specifically, the arm support 3 is movably coupled to the master manipulator handle 2 and the top of the control console, so that it is rotatable in the plane where the top of the control console is located. Further, as shown in FIG. 3, the arm support 3 may be composed of a roughly L-shaped support pole 31 and an arm bracket 32 attached to the end of the support pole 31. Further, a hinge may be provided at the joint between the support pole 31 and the top of the control console, and a slide rail or other components may be provided on the peripheral connecting surfaces between the arm bracket 32 and the master manipulator handle 2, so that the arm support 3 as a whole can rotate about an axis of the connected support pole 31 and arm bracket 32. Preferably, the arm bracket 32 is at least partially configured as an inward recess, which can be designed as a curved recess to match the contour of an arm of an average human operator, so that the recess can receive and support an arm of a human operator.

Optionally, the support pole 31 and the arm bracket 32 may be hinged to each other. The arm bracket 32 as an arm support, after connected to the support pole 31, allows the arm of the human operator to rotate around the table top in a predefined planar scope in virtue of the movable connection between the support pole 31 and the top of the control console. The arm bracket 32 is movably connected, such as hinged, to the support pole 31, so that when the human operator puts his/her arm on the arm bracket 32, his/her arm is allowed to revolve in a predetermined scope about the support pole 31. Thereby, the arm of the human operator can freely move and the operational space is significantly extended. Besides, with the support provided by the arm bracket 32, fatigue accumulated at the arm of the doctor over time during surgery can be reduced. The arm bracket 32 is particularly useful to relax the arm of the doctor.

Figure 4:
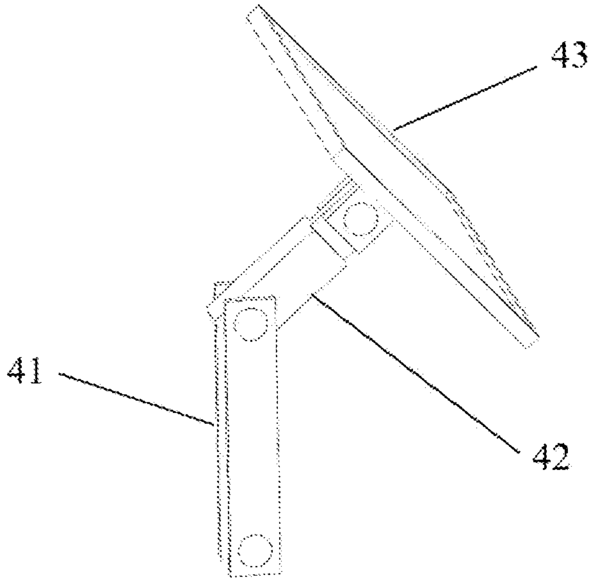
FIG. 4 is a perspective view of a display-and-control portion of the MIS robotic control terminal and robot system according to a preferred mode of the present invention.

According to one preferred mode, as shown in FIG. 4, acting as the core control element of the control console of the present invention, the display-and-control portion 4 may be composed by a first support post 41, a second support post 42, and a touch screen 43. Specifically, the touch screen 43 is connected to the top of the control console through the first support post 41 and the second support post 42 that are movably coupled to each other. Particularly, a storing slot is provided at the center of the top of the control console and matches the touch screen 43 in shape. When the surgical control console is not in use, the touch screen 43 can be stored in the storing slot by adjusting the first support post 41 and the second support post 42. When the control console is used to perform minimally invasive oral surgery, the human operator can use the first support post 41 and the second support post 42 to adjust the relative positions between the touch screen 43 and itself.

According to one preferred mode, the display-and-control portion 4 is for controlling the start/stop of the whole surgical control console and operations of related instruments and components. For a first-time operator who has never used the control console of the present invention before, a personal information account has to be created through the display-and-control portion 4 in advance. Then when the human operator uses the control console, the display-and-control portion 4 can store various operational information by associating the information with the personal information account of the human operator. Particularly, when the human operator later uses the surgical control console again, he/she may first log in his/her personal information account, so that the system will automatically synchronize the operational information stored under the personal information account. For example, initial position information of various surgical instruments can be synchronized, thereby facilitating preoperative setting up of the surgical instruments.

According to one preferred mode, as shown in FIG. 1 and FIG. 2, a multi-axis robotic arm 5 composed of mechanical shafts coupled to each other is provided at one end of the top of the control console, and has its end coupled to a display screen 6. The display screen 6 acts as the main visual interface facing the human operator and can display real-time images in the surgical area captured by the endoscope. Further, the mechanical shafts are movably connected with each other, for example, hinges, and the mechanical shafts can be driven separately. Thus, by driving the mechanical shafts of the multi-axis robotic arm 5, the display screen 6 can be controlled to move in the horizontal and vertical directions, to make the display screen 6 to move up and down, leftward and rightward, and forward and backward, thereby adjusting the relative positions between the display screen 6 and the human operator to fit the operational habits and visual preferences of individual human operators.

According to one preferred mode, during a surgical process, since every master manipulator handle 2 can only control one slave manipulator at one time, the present invention incorporates a foot-operated clutch portion 1 at the bottom of the control console to control switching of the master and slave manipulators. Specifically, the first master handle communication control pedal 11 is mainly used to break signal communication between the first operating handle and the currently controlled slave manipulator. The second master handle communication control pedal 12 is mainly used to break signal communication between the second operating handle and the current controlled slave manipulator. The laser cutter control pedal 13 is mainly used to turn on/off the femtosecond laser cutter. The emergency stop pedal 14 is for triggering emergency stop of moving surgical instruments during a surgical process, so as to secure safety of the surgical process.

According to one preferred mode, during a surgical process, when the pedal for breaking the signal communication of the master and slave manipulators is pressed, the communication signal for controlling the corresponding master and slave manipulators is cut off, so movement of the corresponding master manipulator is no more able to move the coupled slave manipulator. Then the display-and-control portion 4 responds to the corresponding effect. That is, the touch screen 43 displays the control interface of the corresponding master and slave manipulators for the human operator to select a corresponding alternative slave manipulators. At this time, the master manipulator handle 2 comes into signal communication with the newly selected slave manipulator, meaning that switching of the slave manipulator and the master manipulator handle 2 is successful. Particularly, when the first master handle communication control pedal 11 and the second master handle communication control pedal 12 are both pressed, the two master manipulator handles 2 each break the signal communication with at least one slave manipulator coupled thereto, and this indicates that the surgery ends.

Figure 5:
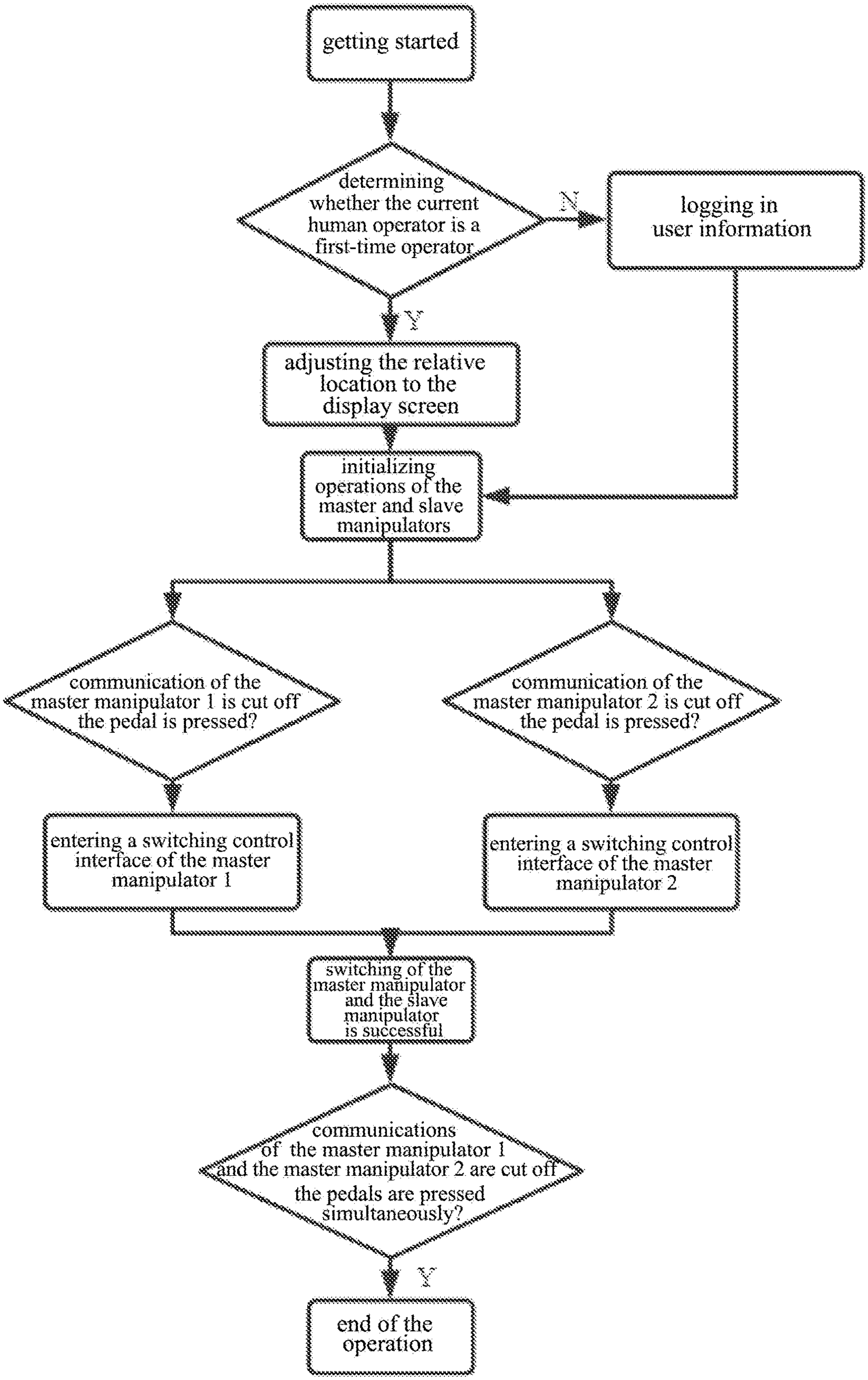
FIG. 5 is a flowchart of operations of the MIS robotic control terminal and robot system according to a preferred mode of the present invention.

According to one preferred mode, FIG. 5 illustrates operational principles of MIS robotic control terminal and robot system of the present invention. Specifically, prior to the surgery, a human operator first enters a corresponding operation control interface through the display-and-control portion 4, and logs in his/her personal information account through the control interface. The system then determines whether the current human operator is a first-time user according to data in the database, and initializes operations of the master and slave manipulators according to the confirmed human operator identity information. Therein, if the current human operator is not a first-time user, the system initializes the spatial locations of the master and slave manipulators by automatically calls the corresponding historical configuration scheme according to the historical operation information of the human operator, so that any human operator who has individual use records does not to make repeat preoperative setting up and preparation each time. If the current human operator is a first-time user, the system stores the identity information of the current human operator into the database. The current human operator can adjust the relative spatial location relationship between himself/herself and the display screen 5 through the display-and-control portion 4, and initialize the spatial location relationship between the master and slave manipulators. The system simultaneously uses various operational records of the current human operator to form a configuration scheme associated with the identity information of the current human operator, so that when the user later logs in again to use the disclosed control console, the system can automatically retrieve a matching configuration scheme according to his/her identity information, so as to eliminate the needs of additional preparation works.

Further, as shown in FIG. 5, after initialization of the master and slave manipulators is done, the human operator may drive or control the master and slave manipulators to operate through the display-and-control portion 4, so as to conduct oral surgery. In this process, when the human operator needs to switch the master and/or slave manipulators, the system will break and confirm the communication states of different control pedals and their respective, corresponding master and slave manipulators according to the braking state of the first master handle communication control pedal 11 or the second master handle communication control pedal 12. Therein, the laser cutter control pedal 13 may be used to directly break communication between the femtosecond laser cutter and its corresponding master manipulator handle 2, and the emergency stop pedal 14 is used to trigger urgent braking of the whole control console and the related surgical instruments during surgery. After the original communication between the master and slave manipulators is cut, the human operator can establish signal communication between the new combination of the master and slave manipulators through the display-and-control portion 4. Furthermore, when the human operator presses the first master handle communication control pedal 11 and the second master handle communication control pedal 12 at the same time, the system takes this as a signal of ending the current surgery, so the communication between each master manipulator handle 2 and the at least one slave manipulator coupled thereto is broken with the current spatial locations held unchanged until a further instruction starts the control console again.

According to one preferred mode, during a surgical process, there may be situations where the human operator wants to use the two master manipulator handles 2 at the two ends of the top of the control console simultaneously or alternately for a surgical operation. In view of surgical safety and use regulations, when the human operator drives at least one slave manipulator, such as a pair of forceps, through the first operating handle coupled thereto, if the human operator further needs to use at least another slave manipulator, such as a femtosecond laser cutter, coupled to the second operating handle to perform related surgical operations, the moving patterns of slave manipulators coupled to master manipulator handles 2 that are different from each other vary with the spacing of the slave manipulators. Specifically, since minimally invasive oral surgery is performed in a relatively special environment where the working area or coverage of the related surgical instruments is very small, any tiny jiggle or deviation can cause significant effect on oral safety of the patient. During a surgical process, the master manipulator handles 2 are used either simultaneously or alternately at high frequency to operate different surgical instruments. For example, there are situations where forceps and a femtosecond laser cutter are to be used together in oral surgery. In this process, when the human operator simultaneously operates two different master manipulator handles 2 to control, for example, a pair of forceps and a femtosecond laser cutter at the same time, the instruments on the two slave manipulators may have physical and functional interference with each other. Therefore, preferably, when a human operator operates slave manipulators of two different master manipulator handles 2 to move simultaneously or alternately, when the operator changes the positions of any master manipulator handle 2 and its corresponding slave manipulator, the system will limit the moving path or moving scope of the slave manipulator according to the distance between the slave manipulator and the slave manipulator corresponding to the other master manipulator handle 2, and according to the types of instruments on the two slave manipulators. Further, limiting the moving path or moving scope of the slave manipulator is done based on surgical instruments information pre-stored in the system database and a scope threshold predetermined according to the operational habit of the human operator or applicable surgical rule. The scope threshold may typically be set by a doctor or an operator according to, for example, surgical experience and surgical regulations.

According to one preferred mode, for example, when the two slave manipulators controlled by two different master manipulator handles 2 are a pair of forceps and a femtosecond laser cutter that is regarded as a safety-crucial surgical instrument. Therefore, when the operator operates the forceps and the femtosecond laser cutter separately, the moving scopes of the two surgical instruments are always kept within a first predetermined interval (e.g., a numerical interval in centimeters). When a trendy that the two surgical instruments come close to each other appears, as their spacing reduces under the control of the human operator, the system decelerates either of the surgical instruments linearly/non-linearly, so as to reduce the probability that the two surgical instruments have physical or functional interference with each other, thereby preventing physical collision or functional interference therebetween from endangering oral safety and personal safety of patients. In other words, the system can, following decrease in the spacing between any two slave manipulators different from each other, slow down any of the moving slave manipulators in a linear/non-linear manner. Particularly, for surgical operations conducted under difficult conditions yet demanding in precision, such as minimally invasive oral surgery, since the space inherently defined by an oral cavity is limited, movements of surgical instruments have to be controlled severely in terms of both moving pattern and path, or physical and functional interference between surgical instruments tend to happen. For example, physical interference like collision can lead to damage to surgical instruments and the broken parts can cause injuries to oral tissues of patients. On the other hand, functional interference such as that the forceps prevents the femtosecond laser cutter from reaching its rays to where treatment is needed can not only degrade surgical efficiency and effects, but also bring about risk that high-power surgical instruments, such as a femtosecond laser cutter, accidentally damages other surgical instruments even without physical contact. All these risks, either to patients or to devices, are undesirable and need to be prevented.

According to one preferred mode, when the two slave manipulators controlled by two different master manipulator handles 2 are, for example a pair of forceps and an endoscope, the moving scopes of the current two surgical instruments is kept within a second predetermined interval (e.g., within a certain numerical interval in millimeters). In other words, based on the types of instruments on the slave manipulators controlled by different master manipulator handles 2, the moving spaces or moving paths of the different slave manipulators controllable to the human operator or allowable by the system is within a predetermined interval, and the moving speed of any slave manipulator is continuously changing with the spacing between itself and another slave manipulator.

According to one preferred mode, based on the types of instruments of any two slave manipulators coupled to two different master manipulators, the human operator controls the moving scopes or moving paths and moving speeds of surgical instruments by any master manipulator and its corresponding slave manipulator according to whether the two slave manipulators are of the same type or not. In the present invention, according to the risk levels of the surgical instruments, the slave manipulators (surgical instruments) used for femtosecond laser minimally invasive oral surgery are classified into Type A slave manipulators, Type B slave manipulators, and Type C slave manipulators. For example, an endoscope is a Type A slave manipulator, a pair of forceps is a Type B slave manipulator, and a femtosecond laser cutter is a Type C slave manipulator. Particularly, the risk levels of the Type A slave manipulators, the Type B slave manipulators, and the Type C slave manipulators are in an ascending order.

According to one preferred mode, if the currently controlled any two slave manipulators coupled to two different master manipulators are a Type A slave manipulator and a Type B slave manipulator, the moving scopes of the current two slave manipulators controllable to the human operator or allowed by the system is within the first moving interval. Or, the spatial locations of the current two slave manipulators are always not smaller than the first spacing. Further, if the current two slave manipulators are a Type A slave manipulator and a Type C slave manipulator, the moving scopes of the current two slave manipulators controllable to the human operator or allowed by the system is within the second moving interval. Or, the spatial locations of the current two slave manipulators are always not smaller than the second spacing. If the current two slave manipulators are a Type B slave manipulator and a Type C slave manipulator, the moving scopes of the current two slave manipulators controllable to the human operator or allowed by the system is within the third moving interval. Or, the spatial locations of the current two slave manipulators are always not smaller than the third spacing.

Preferably, different types of devices connected to the slave manipulators may bring about different levels of risk or damage due to their respective natures. In the present invention, slave manipulators are divided by risk levels corresponding to their types, so as to facilitate human operators or doctors configuring surgical schemes correspondingly and planning and controlling movements of corresponding slave manipulators. This allows strict control of operations of various surgical instruments and their relative spatial locations during minimally invasive oral surgery, thereby minimizing the risk of damage to instruments, devices, and systems, reducing the probability of surgical incidents, and in turn enhancing surgical efficiency and effects.

In other words, based on the actual instrument types on any two slave manipulators coupled to two different master manipulators, when a human operator controls any slave manipulator to move alternately or simultaneously, the moving scope of the current slave manipulator allowable by the system varies depending on the type of the slave manipulator. Preferably, based on the risk levels of slave manipulators of different types, the moving interval and/or spacing may gradually change in a linear/non-linear manner according to the accumulated risk levels. For example, the first spacing between a Type A slave manipulator and a Type B slave manipulator is greater than the second spacing between the Type A slave manipulator and a Type C slave manipulator. Particularly, the moving interval and/or spacing related to the actual instrument types of the slave manipulators may be stored in advance in the system database, and a corresponding data table may be established simultaneously. After a human operator starts the control system of the present invention and establishes signal communication between the master and slave manipulators through the display-and-control portion 4, the system calls the movement schemes included in the data table corresponding the types of the current two slave manipulators from the database according to the actual instrument types of any two slave manipulators currently coupled to two different master manipulators, and uses the called movement schemes to plan the moving path of either of the slave manipulators and limit the moving interval and/or spacing of the current two slave manipulators. Further, during the subsequently minimally invasive oral surgery performed by a human operator using the corresponding slave manipulators, the moving path of either of the slave manipulator always follows the corresponding moving interval and/or spacing.

Preferably, slave manipulators of different risk types are associated with corresponding moving intervals and/or spacing and a related data table or database is established, so that when a human operator starts the system and controls the slave manipulators through the master manipulators to move, the system can limit or plan the moving path for operation of each slave manipulator in advance, thereby ensuring that the individual or synchronous movements of the slave manipulators are always in a certain safe threshold space. limiting or planning the moving path for operation of each slave manipulator in advance can prevent the human operator from breaking the use regulations of the surgical instruments and the surgical rules, thereby eliminating physical or functional conflict or interference between the slave manipulators that causes surgical incidents or damage to the instruments, and minimizing high-risk operations conducted subjectively by the human operator. For example, some human operators may excessively rely on personal surgical experiences or operational habits. In some particular surgical scenarios, forcing two slave manipulators to come close to or separate from each other is likely to cause surgical incidents and damage to instruments. Secondary, for human operators not proficient in operations of instruments and device, the present invention provides an objective and passive way to limit the operational range or space that they operate the surgical instruments on the slave manipulators to move. This not only helps reduce the risk of surgical incidents, but also provides knowledge of regulations for surgical operations and for use of devices by presenting interactive moving spaces and/or spacing when the slave manipulators move around for operators to learn or review. Particularly, practitioners lacking for experience in large surgery can get help and guide that are useful for them to follow and conduct surgery safely in a reasonable operational space. In addition, when an inexperienced or unpracticed human operator uses a robot for oral surgery to conduct corresponding surgical simulation or experiments, he/she can call configuration schemes for slave manipulators from other operators for similar operations through the control console of the present invention as references or templates.

According to one preferred mode, the moving interval and/or spacing between any two slave manipulators of different types may be configured further according to the actual specifications and dimensions of the slave manipulators. Specifically, for forceps of different lengths, weights, and volumes, their moving spaces in a human oral cavity are almost known and fixed. However, due to the factor of dimensions and position relationship between forceps of different sizes and their adjacent or peripheral surgical instruments, their actual moving paths are usually restricted. Particularly, forceps of large sizes have relatively small moving scopes. With the moving distance given, forceps of large sizes are more likely to contact other surgical instruments or even unexpectedly contact oral tissues that are not in the current surgical area than small ones. Preferably, the moving interval and/or spacing related to the actual specifications and dimensions of the slave manipulators may be pre-stored in the database of the system by a human operator, and a data table corresponding thereto can be established as well. After the human operator starts the disclosed control system and establishes signal communication between the master and slave manipulators through the display-and-control portion 4, the system will plan the moving path of either of the slave manipulators and limits the moving interval and/or spacing of the current two slave manipulators according to the specifications and dimensions of the any two slave manipulators currently coupled to the two different master manipulator by means of calling the movement scheme in the data table corresponding to the specifications and dimensions of the current two slave manipulators.

Particularly, the moving interval and/or spacing between any two slave manipulators is configured or divided according to the actual specifications and dimensions, so as to limit the moving path of any slave manipulator more accurately based on the inherent moving spaces of the slave manipulators, and on the basis of the specifications and dimensions and the inherent moving spaces of the slave manipulators, to make full use of the slave manipulators, while preventing them from unexpected contact with other surgical instruments and/or oral tissues or from physical and functional interference, thereby ensuring precise operation and control of various slave manipulators during minimally invasive oral surgery, and reducing the probability of surgical incidents and damages to the instruments.

According to one preferred mode, for operating the femtosecond-laser surgical robot, in the present invention, the foot-operated clutch portion 1 is configured to have an on position, an off position, and at least one intermediate position between or outside the on position and the off position.

Specifically, the off position refers to a spatial location corresponding to the situation that the braking pedal is pressed to a first predetermined position or generates a predetermined travel. In the off state of the off position, the master and slave manipulators are in the idle state, which means that they are mechanically and electrically separated or disconnected. The on position is corresponding to the situation that the braking pedal is not pressed and the slave manipulators are in the working state. Particularly, the intermediate position is determined by the system according to analysis of movements of various operation parts. For example, the central control unit of the system (embedded in the display-and-control portion 4 in the form of software and/or hardware) may set at least a spatial location between or outside the on and off positions according to the displacement/travel of the corresponding braking pedal or transient acceleration that makes the corresponding braking pedal generate a certain displacement/travel. For example, in the process of normal breaking or switching signal communication between the master and slave manipulators, a human operator presses the pedal with a constant, steady speed, and when the human operator abruptly presses the pedal, as this action usually represents an instruction of high priority or importance, it can be defined as an intermediate position. As a further example, after the pedal is pressed to a certain depth, signal communication between the master and slave manipulators is cut off, and further pressing can touch a deeper component there such as a breaker or the like. In this case, the position may act as an intermediate position.

Further, the at least one intermediate position of the foot-operated clutch portion 1 has a first activated state, a second activated state, and a third activated state that are different from each other. For example, the "first activated state" is a "to-be-activated state," and the "second activated state" is a "activated-standby state," while the "third activated state" is a "now-activated state." Different activated states mainly refer to different mechanical and/or electrical connections. For example, the to-be-activated state is a state where the system has mechanical connections ready and is electrically standby. The activated-standby state is a state where the system has electrical preparation done and mechanically standby. The now-activated state is a state where the system has been mechanically and electrically ready, and is about to be activated/started.

According to one preferred mode, the foot-operated clutch portion 1 includes an intrinsic safety braking portion used to perform braking operations on intrinsic safety operations, and a security braking portion used to perform braking operations on dangerous operations. Specifically, the intrinsic safety braking portion may for example include a first master handle communication control pedal 11 and a second master handle communication control pedal 12 of the present invention, which are mainly used to break or switch signal communication between any master manipulator and any slave manipulator. The security braking portion may for example include a laser cutter control pedal 13 and an emergency stop pedal 14, which are mainly for breaking communication of high-risk surgical instruments such as a femtosecond laser cutter and for triggering emergency stop of the control system as a whole. For easy understanding and illustration, an operation related to an intrinsic safety operation is defined as a first operation, and an operation related to a dangerous operation is defined as second operation. Specifically, intrinsic safety operations may include switching master-slave manipulators and stopping movements, and dangerous operations may include operating the femtosecond laser cutter and/or triggering emergency stop of the system.

According to one preferred mode, in the present invention, when one of the master manipulator handles 2 performs a first operation not involving femtosecond laser operations, the neutral positions of the intrinsic safety braking portion and the security braking portion of the foot-operated clutch portion 1 are not activated.

According to one preferred mode, when one of the master manipulator handles 2 performs a second operation related to laser operations, the neutral positions of the intrinsic safety braking portion of the foot-operated clutch portion 1 are in the first activated state. At this time, the intrinsic safety braking portion is in the "to-be-activated state," and the neutral position of the security braking portion of the foot-operated clutch portion 1 is in the second activated state. At this time, the security braking portion is in the "activated-standby state."

In other words, the central control unit of the system can in response to that at least one master manipulator handle 2 is switched from a first operation not related to laser operations to a second operation related to laser operations, or in response to that at least one master manipulator handle 2 performs a second operation related to laser operations, switches the corresponding intrinsic safety braking portion of the foot-operated clutch portion 1 to the neutral position in the first activated state of the intrinsic safety braking portion. Therein, when the intrinsic safety braking portion is at the neutral position in the first activated state, the corresponding intrinsic safety braking portion is in the to-be-activated state.

According to one preferred mode, the central control unit of the system can in response to that at least one master manipulator handle 2 is switched from performing a first operation not related to laser operations to a second operation related to laser operations, or in response to that at least one master manipulator handle 2 performs a second operation related to laser operations, switches the corresponding security braking portion of the foot-operated clutch portion 1 to the neutral position in the second activated state of the security braking portion. Therein, when the corresponding security braking portion is at the neutral position in the second activated state, the corresponding security braking portion is in the activated-standby state.

According to one preferred mode, when one master manipulator handle 2 performs a second operation related to a laser operation and another master manipulator handle 2 performs a first operation not related to a laser operation, the neutral positions of the intrinsic safety braking portion and the security braking portion of the foot-operated clutch portion 1 are both in the second activated state, meaning that the intrinsic safety braking portion and the security braking portion are now both in the "activated-standby state."

According to one preferred mode, when one master manipulator handle 2 performs a second operation related to laser operations and the other master manipulator handle 2 performs a second operation related to laser operations, the neutral position of the foot-operated clutch portion 1 is in the third activated state, which means that the intrinsic safety braking portion and the security braking portion are both in the "now-activated state," and the operation of the master manipulator handle 2 is refused by the system.

According to one preferred mode, the central control unit of the system can according to the state of at least one braking pedal constituting the foot-operated clutch portion 1 and/or the state of at least one the master manipulator handle 2 switches at least one foot-operated clutch portion 1 between the on position and the off position. In the present invention, the security braking portion in the foot-operated clutch portion 1 has at least one neutral position in addition to the on position and the off position, and the security braking portion switches among the on position, the off position, and the at least one neutral position based on the corresponding state determined by the central control unit, so that the security braking portion at least one neutral position can perform braking operations different from dangerous braking operations associated with the off position.

Similarly, the intrinsic safety braking portion of the foot-operated clutch portion 1 has at least one neutral position in addition to an on position and an off position, the intrinsic safety braking portion can be switched among the on position, the off position, and the at least one neutral position by an external force. Therein, the intrinsic safety braking portion is switched by an external force different from the force that switches it to the off position to at least one neutral position, so that the intrinsic safety braking portion performs braking operations different from intrinsic safety operations associated with the off position.

According to one preferred mode, the intrinsic safety braking portion is activated through two ways. One is mechanical activation at the neutral position, which involves that, only when the pedal is further pressed to the extent that a circuit breaker is triggered, can the intrinsic safety braking portion perform braking operations different from intrinsic safety operations associated with the off position. The other is electronic activation at the neutral position, which involves that only when the pedal is pressed at a significant higher speed, can the intrinsic safety braking portion perform braking operations different from the intrinsic safety operation associated with the off position.

According to one preferred mode, in the use of the femtosecond laser device, the intrinsic safety braking portion and the security braking portion can both break electrical and mechanical connections through emergency stop, thereby stopping the system from applying high-power laser beams immediately to prevent incidents, such as irreversible injuries to human bodies caused by improper operations. However, emergency stop indicates mechanical separation between the master manipulator handle 2 and the slave manipulator, and such separation can cause loss of the corresponding motor travel position due to asynchronism at the emergency stop. As a result, the positions and operations recorded by the central control unit of the system become unreliable. Consequently, restoration of devices after emergency stop is always a precious, time- and effort-consuming job. If the patient is now under anesthesia, this means sharply increased surgical risk. In practical use, rather than emergency stop, doctors tend to use relatively conservative approaches in surgery. The optimal surgical position is hard to achieve, and thus final performances of surgical operations vary greatly.

To address this, the present invention creatively divides the foot-operated clutch portion into an intrinsic safety braking portion and a security braking portion. Therein, the intrinsic safety braking portion used to perform braking operations on intrinsic safety operations and the security braking portion used to perform braking operations on dangerous operations each have at least one neutral position. At the neutral position, the central control unit of the system records positions, travels, and postures of various moving components with higher frequency and precision. Thereby, at the neutral position, when an operator presses a corresponding pedal with significantly increased speed or depth, the intrinsic safety braking portion can record the current travel, position, and/or posture while braking the master manipulator handle coupled to the slave manipulator (e.g., a robot gripper), so as to significantly reduce the rebooting time after stop, thereby saving the patient on the operating table from futile waiting.

Additionally, when the security braking portion is in the neutral position, the system is electrically well prepared to stop the femtosecond laser device in any minute by, for example, disconnecting electrical components irrelevant to the current surgical operation in terms of circuit, so as to protect these electrical components from in-rush currents in case of emergency stop. Without such a protective approach, some of these electrical components may be disrupted because a femtosecond laser cutter has a very high instantaneous power, and its sudden stop is destructive if it is not pre-connected a discharge bypass (such as a voltage reducing channel equipped with a tail current diode). For example, for replacing a blown fuse, a time-out for at least ten minutes has to be called during surgery, which introduces additional risk of surgical fault and infection (by, for example, a maintenance technician entering the operating room). Furthermore, having the central control unit of the system disconnect electrical components irrelevant to the current surgical operation in advance also helps reduce inertia faults of the circuits and minimize the downtime. This is of a huge value to enhance the safety of high-risk surgery like femtosecond laser surgery.

According to one preferred mode, the intrinsic safety braking portion and the security braking portion each have a "first activated state," a "second activated state," and a "third activated state" that are different from each other. The activated states of the intrinsic safety braking portion and the security braking portion are associated with the first operations related to intrinsic safety operations and the second operations related to dangerous operations performed by the master manipulator handles 2.

Particularly, when one of the master manipulator handles 2 performs a first operation not involving femtosecond laser operations, the neutral positions of the intrinsic safety braking portion and the security braking portion are not activated. At this time, since the operation is not related to use of a high-risk device, such as a femtosecond laser cutter, and only a single master manipulator handle 2 is performing the corresponding operation, the current operation is of a low risk level, so the neutral positions corresponding to the intrinsic safety braking portion and the security braking portion are not activated. Having the neutral positions not activated means that the central control unit of the system currently has not to prepare for subsequent mechanical and/or electrical disconnection between the master and slave manipulators. Such mechanical and/or electrical preparation involves putting the related components into the activated-standby state, and staying in the activated-standby state means continuous consumption of energy. Since the situation that "one of the master manipulator handles 2 performs a first operation not involving femtosecond laser operations" is related to the minimal risk, excessive pre-preparation is not necessary. This not only eliminates continuous consumption of energy for the system to stay in the activated-standby state, but also reduces loads about unnecessary data collection and computing. In the neutral position, the central control unit of the system records information of the positions, travels, and postures of moving components with higher frequency and precision for facilitating subsequent reboot of the system and restoration of communication of any disconnected surgical instrument based on these recorded positions, travels, and postures, and such information of low-risk surgical instruments such as forceps is of less influence on the progress and safety of the overall surgical process. Even if they are restarted after completely disconnected, data distortion or data loss about this type of surgical instruments due to the current surge happening during reboot is acceptable.

Further, when one master manipulator handle 2 performs the second operation related to a femtosecond laser operation, the neutral position of the intrinsic safety braking portion is in the first activated state, meaning that the intrinsic safety braking portion is now in its "to-be-activated state", and the neutral position of the security braking portion is in a second activated state, meaning that the security braking portion is now in its "activated-standby state." Particularly, since this system involves use of high-risk devices, such as a femtosecond laser cutter, and only a single master manipulator handle 2 is performing the corresponding operation, this operation is of a certain level of safety risk, which is mainly caused by the femtosecond laser cutter. At this time, the intrinsic safety braking portion is in the "to-be-activated state" and the security braking portion is in the "activated-standby state". Since the operation is related to a femtosecond laser cutter, the security braking portion is in the "activated-standby state" that is of higher priority, so as to break the communication between the femtosecond laser cutter and the corresponding master manipulator handle 2 with an increased responding speed. Meanwhile, the intrinsic safety braking portion is in the "to-be-activated state" that is of lower priority. The reason is that, with the preference of not stopping the femtosecond laser cutter directly (e.g., not influence directly generated by the femtosecond laser cutter itself, but influence indirectly generated by another slave manipulator device or influence reflected on the femtosecond laser cutter), it is possible to reduce possible danger and interference that may be reflected on the femtosecond laser cutter by disconnecting and controlling other slave manipulators in a more conservative way using the intrinsic safety braking portion. Whether it be the "to-be-activated state" or the "activated-standby state," since disconnection is well prepared mechanically and/or electrically, the system responds to breakage of communication between the master and slave manipulators is much more efficient than the conventional approach to connection and disconnection in the prior art. This ensures precision and timeliness of overall movement control of surgical instruments. For example, a large time control delay and physical inertia can prevent a surgical instrument from stopping on its expected stop position, and such inaccuracy can be of significant influence in a relatively small surgical environment, such as a human oral cavity.

According to one preferred mode, when both of the at least two master manipulator handles 2 are operating the corresponding slave manipulators, and one of the master manipulator handles 2 performs a second operation involving femtosecond laser operations, the intrinsic safety braking portion and the security braking portion are both in the "activated-standby state" with higher priority. Further, when the at least two master manipulator handles 2 plan to perform corresponding second operations involving femtosecond laser operations, the neutral position of the foot-operated clutch portion 1 is in the third activated state, which means that the intrinsic safety braking portion and the security braking portion are both in the "now-activated state." At this time, the operations of the master manipulator handles 2 are refused by the system. In other words, with the quantity and/or type increase of the slave manipulators to be driven, and accumulation of risk level of the corresponding operations, the activated state corresponding to the neutral position of the intrinsic safety braking portion and/or the security braking portion can vary. This is demonstrated by that as the operational difficulty and the risk level increase, braking operations corresponding to the activated state can be performed with an accordingly increased responding speed.

It should be noted that the above-mentioned specific embodiments are exemplary, and those skilled in the art can come up with various solutions inspired by the disclosure of the present invention, and those solutions also fall within the disclosure scope as well as the protection scope of the present invention. It should be understood by those skilled in the art that the description of the present invention and the accompanying drawings are illustrative rather than limiting to the claims. The protection scope of the present invention is defined by the claims and their equivalents. The description of the present invention contains a number of inventive concepts, such as "preferably", "according to a preferred embodiment" or "optionally", and they all indicate that the corresponding paragraph discloses an independent idea, and the applicant reserves the right to file a divisional application based on each of the inventive concepts.

What is claimed is:

1. A minimally invasive robotic surgery (MIS) robot system, at least comprising:

a master manipulator handle, for driving at least one slave manipulator coupled thereto;

a display-and-control portion, for controlling the master manipulator handle and the at least one slave manipulator coupled to the master manipulator handle; and a foot-operated clutch portion, for breaking signal communication between the master manipulator and the at least one slave manipulator;

wherein when a human operator uses the display-and-control portion to establish signal communication between the master manipulator handle and any of said at least one slave manipulator, the display-and-control portion is at least capable of, according to types of instruments on two said slave manipulators that are currently in communicative connection to master manipulator handles that are different from each other, respectively, defining a moving space of any said slave manipulator in a corresponding surgical area by means of calling movement schemes corresponding to the types of the instruments;

wherein the foot-operated clutch portion comprises an intrinsic safety braking portion for performing braking operations on intrinsic safety operations, the intrinsic safety operations of a low risk level, and a security braking portion for performing braking operations on dangerous operations including performing laser operations or triggering an emergency stop of the MIS robot system, and the intrinsic safety braking portion and the security braking portion are configured to each have at least one neutral position in addition to an on position and an off position, the at least one neutral position used in association with high-power devices, wherein the security braking portion is to be switched among the on position, the off position, and the at least one neutral position based on corresponding states determined by the display-and-control portion, so that the security braking portion at the at least one neutral position is capable of performing the braking operations different from the braking operations on the dangerous operations related to the off position, the at least one neutral position comprising disengagement of at least one of an unused mechanical connection or electrical connection so that when the security braking portion is engaged, damage to the unused mechanical or electrical connection is prevented; and the intrinsic safety braking portion is to be switched from at least one of the on position and the off position to the at least one neutral position by an external-force operation different from an operation that switches it to the off position, so that the intrinsic safety braking portion at the at least one neutral position is capable of performing the braking operations different from the braking operations on the intrinsic safety operations related to the off position;

wherein the display-and-control portion, in response to that at least one said master manipulator handle being switched from a first operation not related to laser operations to a second operation related to laser operations, or in response to that at least one said master manipulator handle performs the second operation related to laser operations, automatically performs at least one of the following operations:

switching the corresponding intrinsic safety braking portion of the foot-operated clutch portion to the neutral position in a first activated state of the intrinsic safety braking portion, where the intrinsic safety braking portion is in a to-be-activated state, and switching the corresponding security braking portion of the foot-operated clutch portion to the neutral position in a second activated state of the security braking portion, where the security braking portion is in an activated-standby state.

2. The MIS system of claim 1, wherein when the human operator uses the display-and-control portion to control any two slave manipulators of said at least one slave manipulator that are in communicative connection to master manipulator handles that are different from each other, respectively, to move, the corresponding moving space of the two slave manipulators allowable by the system are kept within moving intervals and/or moving spacing provided by the movement schemes corresponding to the types of the instruments.

3. The MIS system of claim 2, wherein when the human operator uses the display-and-control portion to control the any two said slave manipulators that are in communicative connection to master manipulator handles that are different from each other, respectively, a travel speed of any one of the two said slave manipulators allowable by the system is associated with spacing between the one of the two said slave manipulators and the other of the two slave manipulators, and the travel speed changes gradually in a linear/non-linear manner with change in a spatial distance between the any two of said at least one slave manipulator.

4. The MIS system of claim 1, further comprising:

arm supports, which are movably coupled to the master manipulator handles, and are used to receive and perform posture adjustment of arms of the human operator;

a multi-axis robotic arm, which is capable of adjusting its own spatial location when driven by the display-and-control portion; and a display screen, which is coupled to the multi-axis robotic arm and is used to display images in a surgical area in a mouth cavity of a patient in a real-time manner.

5. The MIS system of claim 4, wherein the master manipulator handle comprises a first operating handle and a second operating handle provided on a top of a control console such that the first operating handle and/or the second operating handle is configured to have its central axis angled with respect to an edge of the top at a predetermined angle.

6. The MIS system of claim 4, wherein the arm supports are coupled to the master manipulator handle and a top of a control console such that the arm supports are rotatable about the master manipulator handles, wherein the arm support comprises a support pole and an arm bracket that are coupled to each other, wherein the support pole has a support pole end distant from the arm bracket coupled to the top of the control console, and the arm bracket has an arm bracket end distant from the support pole coupled to the master manipulator handle.

7. The MIS system of claim 4, wherein the multi-axis robotic arm is provided on a top of a control console, and includes a plurality of mechanical shafts that are coupled to each other and are to be driven independently, so that the multi-axis robotic arm is capable of moving with at least three degrees of freedom in response to a driving instruction given by the display-and-control portion.

8. The MIS system of claim 1, wherein the display-and-control portion is arranged on a top of a control console, and comprises:

a first support post and a second support post that are movable and are coupled to each other; and a touch screen that provides functions about process control and display;

wherein the first support post is coupled to the top of the control console, and the touch screen is deposited at an end of the second support post.

* * * * *